United States Patent [19]
Macy et al.

[11] Patent Number: 5,958,888
[45] Date of Patent: Sep. 28, 1999

[54] WATER MISCIBLE MACROLIDE SOLUTIONS

[75] Inventors: Lowell R. Macy, Vermillion, S. Dak.; Raymond E. Hopponen, Fort Dodge, Iowa; Roger A. Wilson; James B. Williams, both of Lansdale, Pa.

[73] Assignee: Merial, Inc., Athens, Ga.

[ * ] Notice: This patent is subject to a terminal disclaimer.

[21] Appl. No.: 09/112,690

[22] Filed: Jul. 9, 1998

Related U.S. Application Data

[60] Continuation-in-part of application No. 09/033,146, Mar. 2, 1998, abandoned, which is a division of application No. 08/675,380, Jul. 2, 1996, Pat. No. 5,723,447.

[51] Int. Cl.⁶ .................................................. A61K 31/70
[52] U.S. Cl. ................. 514/29; 514/30; 536/7.1; 536/7.2; 536/7.4
[58] Field of Search .................. 514/29, 30; 536/7.1, 536/7.2, 7.4

[56] References Cited

U.S. PATENT DOCUMENTS 5,175,150   12/1992   Omura et al. .
5,723,447   3/1998    Macy et al. .............................. 514/29

FOREIGN PATENT DOCUMENTS 0 508 699 A1   10/1992   European Pat. Off. .

*Primary Examiner*—Elli Peselev
*Attorney, Agent, or Firm*—Frommer Lawrence & Haug LLP; William S. Frommer; Thomas J. Kowalski

[57] ABSTRACT

Water miscible pharmaceutical compositions containing up to about 40% of a macrolide antibiotic are prepared by reaction of the macrolide with acid in a non-aqueous water miscible organic solvent system.

18 Claims, No Drawings

WATER MISCIBLE MACROLIDE SOLUTIONS

RELATED APPLICATIONS

This application is a continuation-in-part of U.S. application Ser. No. 09/033,146, filed on Mar. 2, 1998, now abandoned, which is in turn a divisional of U.S. application Ser. No. 08/675,380 filed on Jul. 2, 1996, now U.S. Pat. No. 5,723,447, both of which, as well as all documents cited herein and all documents cited in documents cited herein, are hereby incorporated herein by reference.

FIELD OF THE INVENTION

This invention relates to antibiotic compositions suitable for pharmaceutical use and in particular to water miscible solutions of macrolide antibiotics such as erythromycin.

BACKGROUND OF THE INVENTION

Macrolides are a class of antibiotics which contain a many-membered lactone ring to which are attached one or more deoxy sugars. Macrolides are generally bacteriostatic, but have been shown to be bactericidal in high concentration against very susceptible organisms. Macrolides are most effective against gram-position cocci and bacilli, although they do possess some activity against some gram-negative organism. Macrolides exert their bacteriostatic activity by inhibiting bacterial protein synthesis by binding reversibly to the 50 S ribosomal subunit. ("Goodman & Gillman's the Pharmacological Basis of Therapeutics," 9th ed., J. G. Hadman & L. E. Limbird, eds., ch. 47, pp. 1135–1140, McGraw-Hill, N.Y. (1996) ).

The macrolides as a class are colorless and usually crystalline. The compounds are generally stable in near neutral solution, but they only have limited stability in acid or base solutions. The reason for this is because the glycosidic bonds hydrolyze in acid and the lactone ring saponifies in base ("Principles of Medicinal Chemistry," 2nd ed., W. F. Foye, ed., ch. 31, pp. 782–785, Lea & Febiger, Philadelphia (1981) ). Hence, there is a need to prepare stable, water miscible pharmaceutical or veterinary compositions for parenteral, e.g., intravenous, intramuscular, subcutaneous, administration of macrolide antibiotics.

The macrolides are soluble in many organic solvents but are only slightly water soluble. Solutions of macrolides in organic solvent systems are used in human and veterinary practice for administration by the intramuscular and subcutaneous routes. These solutions cannot be used for intravenous administration because the macrolides precipitate when the solution is introduced into an aqueous medium as into body fluids. Aqueous solutions of salts of macrolides can be prepared but such solutions have such limited stability as to be limited to use for only a short time period after preparation.

A water miscible solution of macrolides which would be stable for an extended period of time would be of great value to both the medical and veterinary professions. It could be used for intravenous administration to rapidly provide therapeutic blood levels for more effective treatment of infectious diseases. A water miscible solution would also allow for more rapid absorption from intramuscular and subcutaneous injection sites leading to higher concentrations in body fluids and more effective control of infectious diseases. Such a solution would also be useful for oral administration to poultry and swine in their drinking water.

SUMMARY OF THE INVENTION

The present invention provides a stable, high potency water miscible formulation of macrolides. The macrolides as a class contain at least one basic nitrogen group which can be converted in non aqueous solutions into stable water miscible compositions by the addition of an acid. The resulting compositions are stable for extended periods of time and do not lead to precipitation of the macrolide when introduced into an aqueous environment. The acid is added in an amount about equimolar to the number of available nitrogens present. For example, an acid advantageously is added in an amount at least equimolar to the erythromycin as erythromycin only contains one available nitrogen. Solutions containing as much as 40% of the macrolide can be prepared in this manner.

These and other embodiments are disclosed or are obvious from and encompassed by, the following Detailed Description.

DETAILED DESCRIPTION

Macrolides as a class include the erythromycin and its derivative as well as other derivatives such as the azalides. Erythromycin (MW 733.94 daltons) is the common name for a macrolide antibiotic produced by the growth of a strain of *Streptomyces erythreous*. It is a mixture of three erythromycins, A, B and C consisting largely of erythromycin A which is represented by the formula:

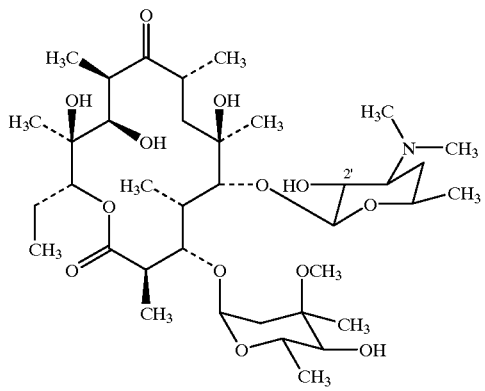

Its chemical name is (3R*, 4S*, 5S*, 6R*, 7R*, 9R*, 11R*, 12R*, 13S*, 14R*) -4-[(2,6-dideoxy-3-C-methyl-3-O-methyl-α-L-ribo-hexopyranosyl)-oxy]-14-ethyl-7,12,13-trihydroxy-3,5,7,9,11,13-hexamethyl-6[[3,4,6-trideoxy-3-(dimethylamino)-β-D-xylo-hexapyranosyl]oxy] oxacyclotetradecane-2, 10-dione, ($C_{37}H_{67}NO_{13}$)

Erythromycin has a broad and essentially bacteriostatic action against many Gram-positive and some Gram-negative bacteria as well as other organisms including mycoplasmas, spirochetes, chlamydiae and rickettsiae. In humans, it finds usefulness in the treatment of a wide variety of infections. It finds wide application in veterinary practice in the treatment of infectious diseases such as pneumonias, mastitis, metritis, rhinitis, and bronchitis in cattle, swine and sheep.

Other derivatives of erythromycins include carbomycin, clarithromycin, josamycin, leucomycins, midecamycins, mikamycin, miokamycin, oleandomycin, pristinamycin, rokitamycin, rosaramicin, roxithromycin, spiramycin, tylosin, troleandomycin, and virginiamycin. As with the erythromycins, many of these derivatives exist as component mixtures. For example, carbomycin is a mixture of carbomycin A and carbomycin B. Leucomycin exists as a mixture of components $A_1$, $A_2$, $A_3$, $A_9$, $B_1$–$B_4$, U and V in various proportions. Component $A_3$ is also known as josamycin and leucomycin V is also known as miokomycin. The major components of the midecamycins is midecamycin A and the minor components are midecamycins $A_2$, $A_3$ and $A_4$. Likewise, mikamycin is a mixture of several components, mikamycin A and B. Mikamycin A is also known as virginiamycin $M_1$. Pristinamycin is composed of pristinamycins $I_A$, $I_B$, and $I_C$, which are identical to virginiamycins $B_2$, $B_{13}$ and $B_2$ respectively, and pristinamycin $II_A$ and $II_B$, which are identical to virginiamycin $M_1$ and 26,27-dihydrovirginiamycin $M_1$. Spiramycin consists of three components, spiromycin I, II, and III. Virginiamycin is composed of virginiamycin $S_1$ and virginiamycin $M_1$. All these components may be used in this invention. Sources of these macrolides are well known to the practitioner and are described in the literature in references such as "The Merck Index," 12th ed., S. Budarari, ed., Merck & Co., Inc., Whitehouse Station, N.J. (1996).

The azalides are semisynthetic macrolide antibiotics related to erythromycin A and exhibit similar solubility characteristics. The structure of azithromycin is:

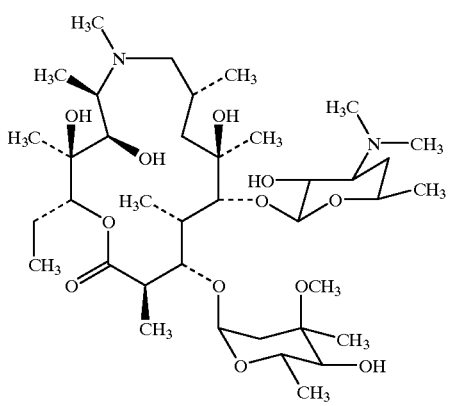

Compounds termed herein formula I and formula II have the following structures:

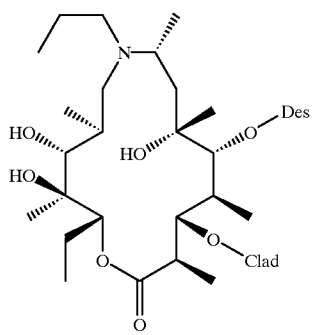

wherein Des is desosomine and Clad is cladinose (formula I) and

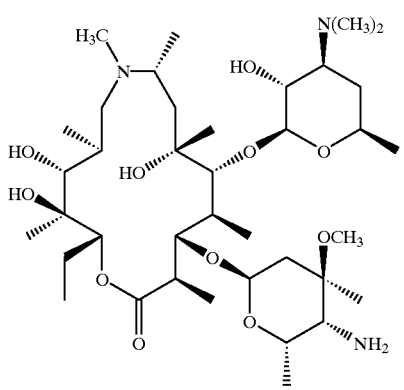

(formula II). These compounds are disclosed in EP 508699, herein incorporated by reference. The corresponding basic and acid addition salts and ester derivatives of the macrolides compounds are also contemplated. These salts are formed from the corresponding organic or inorganic acids or bases. These derivatives include the customary hydrochloride and phosphate salts as well as the acetate, propionate and butyrate esters. These derivatives may have different names. For example, the phosphate salt of oleandomycin is matromycin and the triacetyl derivative is troleandomycin. Rokitamycin is leucomycin V 4-B-butanoate, 3B-propionate. When using these forms to prepare the inventive compositions, more or less acid may have to be added so that final amounts of acid in solution is approximately equal molar to the number of nitrogen atoms present in the molecule.

The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. organic acids include all pharmaceutically or veterinary acceptable aliphatic, alicyclic and aromatic carboxylic acids, dicarboxylic acids tricarboxylic acids and fatty acids. Preferred acids are straight chain or branched, saturated or unsaturated $C_1$–$C_{20}$ aliphatic carboxylic acids, which are optionally substituted by halogen or by hydroxyl groups, or $C_6$–$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

A variety of organic solvents or mixtures of solvents can be used as the vehicles for the compositions. The solvents contemplated are those water miscible organic solvents in which the macrolides are soluble and which are commonly acceptable in the pharmaceutical and veterinary fields to practitioners of those arts. Such compounds include alcohols, diols, triols, esters, amides, and ethers. Examples of suitable solvents that can be used include: methanol, ethanol, propanol, butanol, glycerol, propylene glycol;

polyglycols such as polyethylene glycol 200, polyethylene glycol 300 and polyethylene glycol 400; pyrrolidones such as N-methyl pyrrolidone and 2-pyrrolidone; glycol ethers such as propylene glycol monomethyl ether, dipropylene glycol monomethyl ether and diethylene glycol ethyl ether. Other solvents include di(ethylene glycol)ethyl ether (transcutol), di(ethylene glycol)ethyl ether acetate, dimethyl isosorbide (Arlasolve DMI), di(propylene glycol)methyl ether (Dowanol DPM), di(propylene glycol)methyl ether acetate, glycerol formal, glycofurol, isopropylidene glycerol (Solketal), isopropyl myristate, N,N,-dimethyl acetamide, PEG 300, propylene glycol, and triacetin. Esters may also be used. Polar, aprotic solvents such as DMSO can also be used.

Compositions of the present invention can be readily prepared by adding an amount of acid which is equal molar to the number of nitrogen groups present in the macrolide. For example, if there are three nitrogen groups, a total of approximately 2.7 to 3.3 moles of acid are used. Where there are two nitrogen groups present, a total of approximately 1.8 to 2.2 moles of acid is added. For erythromycin, which has one nitrogen group, a total of approximately 0.9 to 1.1 moles of acid is used. For example, when preparing a composition containing erythromycin as the macrolide, acetic acid is first added in an amount about equimolar to the desired concentration of erythromycin to the selected organic solvent or solvents. The erythromycin is then added and the mixture stirred until complete solution results. Other macrolides are prepared in a similar manner.

Thus, the invention relates to a stable water miscible a macrolide antibiotic composition comprising: a) a macrolide antibiotic or a derivative thereof at a concentration of between about 10% and about 40% by weight, based on the volume of the composition; b) an acid present in an amount about equimolar to the number of available nitrogen groups present in the macrolide and forming a water soluble acetate compound of the macrolide; and c) a water miscible non-aqueous vehicle composed of a suitable organic solvent or mixture of solvents.

Advantageously, the macrolide erythromycin is in the form of a base. Especially preferred is where the macrolide is erythromycin and it is present in its base form.

The composition is advantageously provided in the form of a sterile injectable composition.

The macrolide preferably is present in a concentration of between about 20% and about 30% by weight based on the volume of the composition.

The vehicle advantageously is composed of propylene glycol monomethyl ether, or dipropylene glycol monomethyl ether, or diethylene glycol ethyl ether, or mixtures thereof. Advantageously, the vehicle is composed of N-methyl pyrrolidone in a concentration of between about 30% and about 50% by volume and the balance is propylene glycol. Preferably, the vehicle is composed of N-methyl pyrrolidone in a concentration of between about 30% and about 50% by volume and the balance is polyethylene glycol 200, or polyethylene glycol 300 or polyethylene glycol 400.

The invention especially relates to a stable water miscible erythromycin composition comprising: a) erythromycin at a concentration of between about 10% and about 40% by weight, based on the volume of the composition; b) acetic acid present in an amount at least equimolar to that of the erythromycin and forming a water soluble acetate compound of erythromycin; and c) a water miscible non-aqueous vehicle composed of a suitable organic solvent or mixture of solvents.

The invention further relates to a method of preparing a stable, high potency water miscible macrolide antibiotic composition comprising the steps of: a) preparing a non-aqueous vehicle of a water miscible organic solvent or solvents; b) adding the acid in an amount so that the total concentration of acid is approximately equal molar to the number of free nitrogen groups present in the macrolide with respect to the desired concentration of the macrolide; and c) combining the acid solution with the macrolide in order to achieve a final concentration of between about 10% and about 40% by weight of the macrolide.

A better understanding of the present invention and of its many advantages will be had from the following example, given by way of illustration.

EXAMPLE

One liter of a 20% solution of erythromycin was prepared according to the following procedure:
Erythromycin (based on a potency of 910 micrograms per milligram)

| | |
|---|---|
| $\frac{200g}{0.910}$ = | 219.8 g |
| Glacial acetic acid | 16.4 g |
| N-methyl pyrrolidone | 400.0 mL |
| Propylene glycol | qs 1000.0 mL |

The glacial acetic acid was added to a mixture of the N-methyl pyrrolidone and 300 mL of propylene glycol and mixed. The erythromycin was added slowly with stirring. When the erythromycin was completely dissolved, the solution was brought to volume with propylene glycol.

The above description of the invention is intended to be illustrative and not limiting. Various changes or modification in the embodiment described may occur to those skilled in the art. These can be made without departing from the scope or spirit of the invention.

\* \* \*

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A stable water miscible macrolide antibiotic composition comprising:
   a) a macrolide antibiotic at a concentration of between about 10% and about 40% by weight, based on the volume of the composition;
   b) an acid present in an amount about equimolar to the number of available nitrogen groups present in the macrolide and forming a water soluble salt compound of the macrolide; and
   c) a water miscible non-aqueous vehicle composed of a veterinary or pharmaceutically acceptable organic solvent or mixture of solvents, wherein the macrolide antibiotic is ervthromycin, an azalide, carbomycin, clarithromycin, josamycin, leucomycins, midecamycins, mikamycin, miokamycin, oleandomycin, pristinamycin. rokitamycin, rosaramicin, roxithromycin spiromycin, tylosin. troleandomycin or virainiamycin or a derivative of these antibiotics.

2. A composition according to claim 1, wherein the macrolide antibiotic is selected from the group consisting of erythromycin and a derivative thereof.

3. A composition according to claim 1 wherein the erythromycin is in the form of an erythromycin base.

4. A composition according to claim 1 wherein the composition is provided in the form of a sterile injectable composition.

5. A composition according to claim 1 wherein the macrolide antibiotic is present in a concentration of between about 20% and about 30% by weight based on the volume of the composition.

6. A composition according to claim 1 wherein the vehicle is composed of propylene glycol monomethyl ether, or dipropylene glycol monomethyl ether, or diethylene glycol ethyl ether, or mixtures thereof.

7. A composition according to claim 1 wherein the vehicle is composed of N-methyl pyrrolidone in a concentration of between about 30% and about 50% by volume and the balance is propylene glycol.

8. A composition according to claim 1 wherein the vehicle is composed of N-methyl pyrrolidone in a concentration of between about 30% and about 50% by volume and the balance is polyethylene glycol 200, or polyethylene glycol 300 or polyethylene glycol 400.

9. A composition according to claim 1, wherein the acid is selected from the group consisting of acetic acid, propionic acid, isopropionic acid, butyric acid, iso-butyric acid, sec-butyric acid, and valeric acid.

10. A composition according to claim 1, wherein the solvent is N-methyl pyrrolidone.

11. A method of preparing a stable, high potency water miscible macrolide antibiotic composition comprising the steps of:
   a) preparing a non-aqueous vehicle of a water miscible organic solvent or solvents;
   b) adding acid in a concentration so that the total amount of acid is approximately equimolar to the number of free nitrogen groups present in the macrolide with respect to the desired concentration of the macrolide; and
   c) combining the acid solution with the macrolide in order to achieve a final concentration of between about 10% and about 40% by weight of the macrolide in order to achieve a final concentration of between about 10% and about 40% by weight of the macrolide,
   wherein the macrolide antibiotic is erythromycin, an azalide, carbomycin, clarithromycin. josarnycin, leucomycins, midecamycins, mikamycin, miokamycin, oleandomycin. pristinamycin, rokitamycin. rosaramicin, roxithromycin, spiromycin, tylosin, troleandomycin and virginiamycin or a derivative of these antibiotics.

12. A stable water miscible azalide macrolide antibiotic comprising:
   a) an azalide at a concentration of between about 10% and about 40% by weight, based on the volume of the composition;
   b) an acid present in an amount about equimolar to the number of available nitrogen groups present in the azalide and forming a water soluble salt compound of the azalide; and
   c) a water miscible non-aqueous vehicle composed of a veterinary or pharmaceutically acceptable organic solvent or mixture of solvents.

13. A composition according to claim 12, wherein the azalide is azithromycin or is of the formula

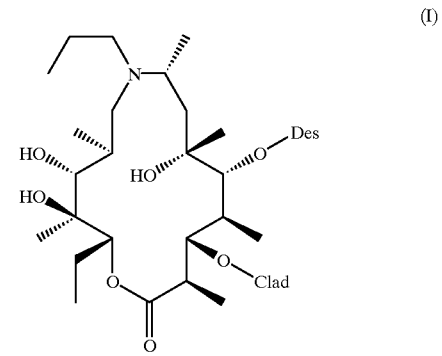

(I)

wherein Des is desosomine and Clad is cladinose or

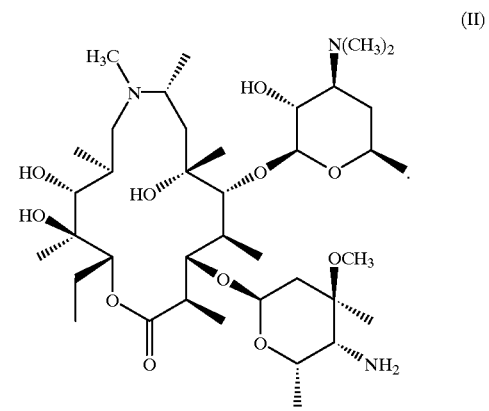

(II)

14. A composition according to claim 12, wherein the azalide is

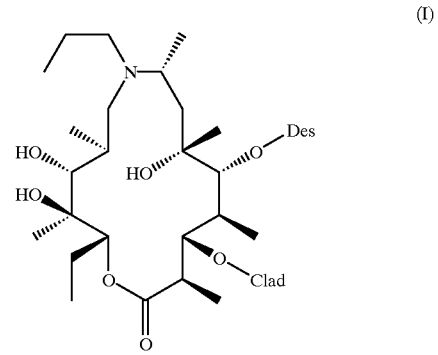

(I)

wherein Des is desosomine and Clad is cladinose or

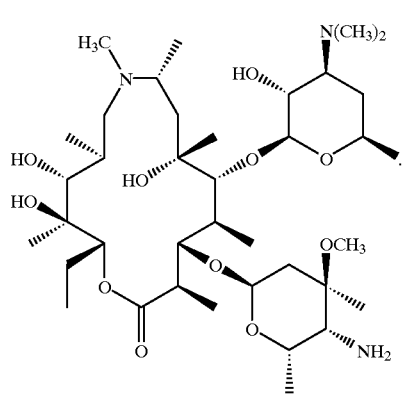

15. A composition according to claim 12, wherein the azalide is present in a concentration of between about 20% and about 30% by weight based on the volume of the composition and the vehicle is composed of propylene glycol monomethyl ether, or dipropylene glycol monomethyl ether, or diethylene glycol ethyl ether, or mixtures thereof.

16. A composition according to claim 12, wherein the vehicle is composed of N-methyl pyrrolidone in a concentration of between about 30% and about 50% by volume and the balance is polyethylene glycol 200, or polyethylene glycol 300 or polyethylene glycol 400.

17. A composition according to claim 12, wherein the acid is selected from the group consisting of acetic acid, propionic acid, isopropionic acid, butyric acid, iso-butyric acid, sec-butyric acid, and valeric acid.

18. A stable water miscible azalide macrolide antibiotic composition comprising:
   a) azithromycin, or an azalide of the formula:

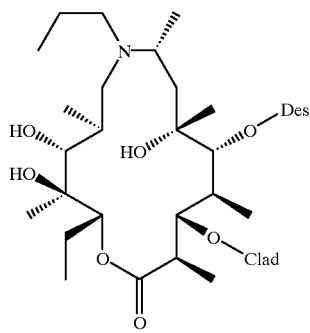

wherein Des is desosomine and Clad is cladinose or

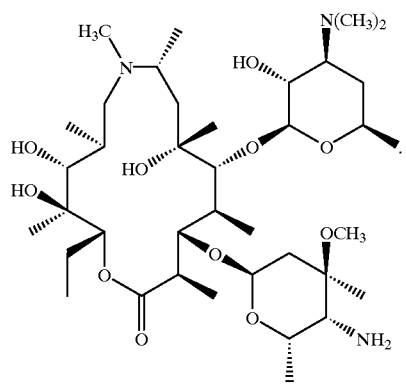

at a concentration of between about 10% and about 40% by weight, based on the volume of the composition;
   b) acetic acid present in an amount at least equimolar to the number of free nitrogen atoms present in the azalide macrolide and forming a water soluble acetate compound of azalide macrolide; and
   c) a water miscible non-aqueous vehicle composed of a suitable organic solvent or mixture of solvents.

* * * * *